United States Patent [19]

Buysch et al.

[11] 4,044,058

[45] Aug. 23, 1977

[54] PROCESS FOR THE PREPARATION OF α,α,α',α'-TETRAMETHYLPHENYLENE BISCARBINOLS

[75] Inventors: Hans-Josef Buysch, Krefeld-Bockum; Jürgen Heuser, Krefeld, both of Germany

[73] Assignee: Bayer Aktiengesellschaft, Germany

[21] Appl. No.: 617,381

[22] Filed: Sept. 29, 1975

[30] Foreign Application Priority Data

Oct. 4, 1974 Germany .............................. 2447346

[51] Int. Cl.$^2$ ....................... C07C 29/00; C07C 27/10
[52] U.S. Cl. .................................. 260/618 C; 260/592
[58] Field of Search ..................................... 260/618 C

[56] References Cited

U.S. PATENT DOCUMENTS

| | | | |
|---|---|---|---|
| 2,438,125 | 3/1948 | Lorand et al. | 260/618 C |
| 2,548,435 | 4/1951 | Lorand et al. | 260/618 C |
| 3,402,205 | 9/1968 | Gregory | 260/618 C |
| 3,420,893 | 1/1969 | Faltings et al. | 260/618 C |
| 3,555,101 | 1/1971 | Buysch et al. | 260/618 C |
| 3,567,786 | 3/1971 | Bostian et al. | 260/618 C |

*Primary Examiner*—Norman Morgenstern
*Attorney, Agent, or Firm*—Connolly and Hutz

[57] ABSTRACT

An improved process for the preparation of an α, α, α' ,α'-tetramethyl-phenylene-biscarbinol by the oxidation of at least one diisopropyl benzene with air or oxygen at elevated temperatures in the presence of an aqueous solution of a strong alkali, the improvement comprises carrying out the oxidation with a carbinol content of at least 52% by weight in the organic phase and an alkali concentration of at least 8% by weight based on the aqueous phase and 1 to 10% by weight based on the organic phase.

6 Claims, No Drawings

PROCESS FOR THE PREPARATION OF α,α,α',α'-TETRAMETHYLPHENYLENE BISCARBINOLS

This invention relates to a process for the preparation of α,α,α',α'-tetramethyl-phenylene-biscarbinols, which will hereinafter be referred to as biscarbinols, with a low hydroperoxide and ketone content by the oxidation of diisopropyl benzenes with air or oxygen at elevated temperatures in the presence of strong aqueous alkalis.

Biscarbinols are important starting materials for the preparation of bisphenols and aromatic diamines which in turn are used for the production of linear thermoplastic polycondensates, for example polycarbonates, polyurethanes, novalaks or resols. Highly alkylated bisphenols are very effective stabilisers for polyurethanes.

When used for these purposes, the biscarbinols must be exceptionally pure. Contamination with hydroperoxides and carbonyl compounds must be particularly avoided. The latter are formed in side reactions during the oxidation process and consist mainly of acetophenone derivatives. If these impurities are present in quantities of only a few percent by weight, they have a harmful effect on the properties of the resulting polycondensation products. Resols and resites, for example, cause discolourations and a deterioration in the mechanical properties. Complicated purification processes involving considerable losses are necessary for removing these unwanted byproducts. The purification also results in a loss of biscarbinol yield.

It is known to prepare biscarbinols by the atmospheric oxidation of diisopropyl benzene in the presence of strong aqueous alkalis. According to British patent specification No. 681,990, carbinols are obtained in the presence of preferably 2 to 8 percent by weight of alkalis in the aqueous phase with the aid of catalysts such as active charcoal. Oxidations carried out in this way, however, give rise to a biscarbinol which is heavily contaminated with acetophenone derivatives and completely useless for the purposes mentioned above. To prevent the presence of these high proportions of ketones, it has been proposed in German Auslegeschrift No. 1,253,692 to carry out the oxidation of diisopropyl benzenes at alkali concentrations of at least 40 percent by weight, preferably 60 percent by weight, based on the aqueous phase and about 20 percent by weight, preferably 40 percent by weight based on the organic phase. This measure does in fact reduce the hydroperoxide and ketone content.

The employment of such highly concentrated alkalis has, however, serious disadvantages. If oxidation is continued to higher conversion rates, reaction mixtures with high viscosities are obtained. The gas used for oxidation does not become evenly and rapidly distributed in such viscous mixtures and consequently the reaction velocity falls far below the initially determined rate of oxidation. However, high conversions are necessary for economic reasons. The process described in German Auslegeschrift No. 1,253,692 is not suitable for this purpose. Moreover, if the process is carried out continuously, for example with a biscarbinol content of 15%, the large quantities of alkali, about 1.5 to 1.8 kg of alkali metal hydroxide per kg of biscarbinol, must be recovered not only for economic reasons but also to prevent environmental pollution. The alkalis must be freed from byproducts such as carbonates and sodium salts of carboxylic acids and then concentrated by removal of the water of reaction. This can be achieved, if at all, only by extremely expensive processes.

Moreover, according to the above mentioned Auslegeschrift, efficient oxidation requires an excess of oxygen to be constantly present. This again requires a high rate of flow of air on the use of air enriched with oxygen. In that case it is difficult to avoid the presence of explosive mixtures in the vapour space.

It has not been found that the oxidation of diisopropyl benzenes with air or oxygen in the presence of strong aqueous alkalis at elevated temperatures leads to products which are practically free from hydroperoxides and ketones if the organic phase contains at least 52% by weight of carbinol and the concentration of strong alkalis is at least 8% by weight, preferably from 9 to 30% by weight, based on the aqueous phase and 1 to 10% by weight, based on the organic phase.

The present invention therefore relates to an improved process for the preparation of α,α,α',α'-tetramethyl-phenylene-biscarbinols by the oxidation of optionally substituted diisopropyl benzenes with air or oxygen at elevated temperatures in the presence of aqueous solutions of strong alkalis, the improvement comprises carrying the oxidation out with a monocarbinol and/or biscarbinol content of at least 52% by weight in the organic phase and a concentration of alkalis of at least 8% by weight, based on the aqueous phase and 1 to 10% by weight, based on the organic phase.

That the biscarbinols obtained by the process according to the invention are virtually free from byproducts is all the more surprising in view of the fact that, according to the teaching of British patent specification No. 681,990, the formation of ketones when hydrocarbons are converted to an extent of 40 to 50% is promoted by the oxidative degradation of carbinols.

The inventive process has the following advantages over the known art:

Owing to the low viscosity of the reaction mixture, its conversion may rise very high, up to or over 90% without oxidation becoming too slow and therefore uneconomic. A high volume/time yield is therefore obtained.

The gas used for oxidation can be fed in at such a rate that all the oxygen is used up and the exhaust gas is therefore free from oxygen and hence non-explosive. If desired, however, oxidation may also be carried out with an oxygen excess.

The recovery and delivery of the oxidation mixture through pumps and pipes is also facilitated because of the low viscosity of the reaction mixture obtained by using dilute alkalis.

Purification and concentration of the aqueous waste liquor is uneconomic owing to the small quantities of alkali involved it can, however, be carried out with much simpler means and at lower cost than if large quantities of alkali are present. Contamination of the effluent water is also greatly reduced since only about 0.04 to 0.07 kg of sodium hydroxide are used per kg of biscarbinol.

Suitable starting compounds for the process according to the invention are m- and p-diisopropyl benzene, α-hydroxy-m- and -p-diisopropyl benzene and mixtures of these compounds. Distillation fractions from the propylation of benzene, which in addition to at least 50% by weight and preferably 75% by weight of diisopropyl benzene also contain other propylation products or byproducts such as cumene, trimethyl indane, phenyl hexane or phenyl butane are also suitable.

The alkalis used may be sodium hydroxide and potassium hydroxide.

The process may be carried out discontinuously, but is particularly suitable for continuous operation because the most suitable reaction conditions for the invention can then be adjusted more easily.

Studies have shown that the more advanced the degree of oxidation and hence the higher the carbinol content, the smaller can be the quantity of concentration of alkali used. A continuous operation to high conversions therefore means that only small quantities of alkalis need be used, and consequently the process is easier to carry out.

The reaction temperature employed is preferably between 75° and 145° C, more preferably between 90° and 120° C. Oxidation is preferably carried out at a pressure of from 1 to 50 bar. No significant improvement is obtained by employing pressures above 50 bar.

Alkali is used up by the oxidation byproducts such as carbon dioxide and carboxylic acids during oxidation and must be replaced, preferably in a concentrated form since it gets diluted to the required concentration by the water present and the water formed in the reaction. However, the alkalis may be added in a concentrated, solid or dilute form.

The supply of air or oxygen into the reaction mixture is carried out by known methods, either using frits or inlet tube in bubble columns or with the aid of stirring, preferably with the use of gasification stirrers which ensure efficient distribution of gases in liquids.

EXAMPLE 1

Oxygen is introduced into 1500 g of a mixture of 476 g of fresh diisopropyl benzene, consisting of about 40% of p- and about 60% of m-diisopropyl benzene and 1024 g of a mixture of 216 g of diisopropyl benzene and 808 g of $\alpha,\alpha'$-dimethyl-isopropyl phenyl carbinol which has been isolated from a previous batch and 390 g of a 35% sodium hydroxide solution at 100° to 110° C. A gasification stirrer in the form of a cross blade agitator with a hollow axial shaft rotating at about 500 to 600 revs per min is used for introducing the oxygen. More oxygen is added at the rate at which it is consumed so that no waste gas is formed. Oxidation is stopped after 20 hours. The organic phase contains 15% of diisopropyl benzene, 41% of monocarbinol, 44% of biscarbinol and 0.1% each of acetophenone derivatives and active oxygen. The aqueous phase contains 15% of sodium hydroxide. The remainder is neutralised with silicic acid (from the glass) and oxidation byproducts. The quantity of alkali is therefore about 4% by weight, based on the organic phase. The yield of biscarbinol is 91% of the theory, based on the degree of conversion of the hydrocarbons.

EXAMPLE 2 a. Diisopropyl benzene is continuously oxidised with air to biscarbinol in a pressure reactor equipped with a hollow shaft gasification stirrer. The temperature is 100° C and the pressure 20 bar.

The concentration of the various components in the organic phase when a steady state has been reached is 30% of diisopropyl benzene, 51% of $\alpha,\alpha$-dimethyl-isopropyl phenyl carbinol, 19% of biscarbinol and 0.2% of each of acetophenones and active oxyen. The aqueous phase has an NaOH content in the steady state of 25%. The proportion of organic phase to aqueous phase is 1 : 0.165, which corresponds to about 4% of sodium hydroxide based on the organic phase.

To obtain these concentrations at a production rate of 13 kg of biscarbinol per hour, 10 Nm$^3$ of pressurised air, 33.5 kg of diisopropyl benzene, 35 kg of $\alpha,\alpha$-dimethyl-isopropyl phenyl carbinol and 7 kg of 35% sodium hydroxide are added per hr. The corresponding quantity of crude oxidation product is continuously removed from the reactor. The exhaust gas contains less than 1% of oxygen.

b. The biscarbinol obtained according to example 1 is condensed with phenol as follows:

A mixture of 194 g of biscarbinol (1 mol), 752 g (8mol) of phenol and 10 ml of 85% phosphoric acid are heated to a reaction temperature of 80° C at reduced pressure with stirring while the water of reaction is distilled off. After a reaction time of 2 hours, all the water has been removed and a pressure of 25 Torr has been reached. After a further 6 hours, 8.8 ml of concentrated sodium hydroxide solution are added and phenol is distilled off at 210° C and 10 Torr. 278 g of a clear, light-coloured hard resin which has a phenolic hydroxyl content of 7.5 and a colour index number of 0 is obtained.

The colour index number was taken from the iodine scale and determined on a 50% solution of the resin in n-butanol.

c. 200 g of 30% formalin solution are added to a solution of 278 g of the condensation resin obtained according to (b) in 556 g of butanol at a pH of 8 to 9 and the mixture is heated to 91° to 93° C for 8 hours. After the addition of 200 g of water, the reaction mixture is adjusted to pH 4 by the addition of a few drops of phosphoric acid to facilitate phase separation and the lower (aqueous) phase is separated off at 60° C. After separation of the phases at 60° C, the organic phase is dehydrated azeotropically, evaporated to the desired solid content and filtered. The yield was 530 g of 60% resol resin in butanol.

After the addition of 0.5% of a 10% solution of phosphoric acid and 3% of Maprenal NP$^{(R)}$ the resol resin is mixed with an equal quantity of epoxide resin Epikote 1007 (shell), applied to metal sheets and stoved at 180° C for 12 minutes. A colourless coating which is capable of being deep-drawn and sterilised and is extremely resistant to chemicals is obtained.

EXAMPLE 3

This example is carried out in a similar manner to example 2, with the exception that the carbinol concentrations are higher, that is to say 48% of $\alpha,\alpha$-dimethyl-isopropyl phenyl carbinol and 43% of biscarbinol. The sodium hydroxide concentration is kept at 9%, based on the aqueous phase, corresponding to about 1.5% of alkali, based on the organic phase. When this procedure is employed, the concentration of acetophenone derivatives in the steady state of 0.30%. The exhaust gas contains less than 1% of oxygen.

We claim:

1. In the process for the preparation of an $\alpha,\alpha,\alpha',\alpha'$-tetramethyl-phenylene-biscarbinol by the oxidation of at least one diisopropyl benzene with air or oxygen at elevated temperatures in the presence of an aqueous solution of a strong alkali, the improvement comprising carrying out the oxidation with a monocarbinol and/or biscarbinol content of at least 52% by weight in the organic phase and an alkali concentration of 9 to 30% by weight based on the aqueous phase and 1 to 10% by weight based on the organic phase.

2. A process as claimed in claim 1 wherein the diisopropyl benzene is m- or p-diisopropyl benzene, α-hydroxy-m- and p-diisopropyl benzene or a mixture thereof.

3. A process as claimed in claim 1, wherein the alkali is sodium or potassium hydroxide.

4. A process as claimed in claim 1, wherein the reaction temperature is from 75° to 145° C.

5. A process as claimed in claim 4 wherein the reaction temperature is from 90° to 120° C.

6. A process as claimed in claim 1, wherein the oxidation is carried out at a pressure of from 1 to 50 bar.

* * * * *